United States Patent [19]

Birngruber

[11] Patent Number: 5,302,259
[45] Date of Patent: Apr. 12, 1994

[54] METHOD AND APPARATUS FOR ALTERING THE PROPERTIES IN LIGHT ABSORBING MATERIAL

[76] Inventor: Reginald Birngruber, Veilchenweg 48, 8028 Taufkirchen, Fed. Rep. of Germany

[21] Appl. No.: 22,773

[22] Filed: Feb. 23, 1993

Related U.S. Application Data

[63] Continuation of Ser. No. 693,678, Apr. 30, 1991, abandoned.

[51] Int. Cl.$^5$ ................................. C25F 5/00
[52] U.S. Cl. ................. 204/131; 204/157.61; 204/901
[58] Field of Search ........... 204/901, 157.61, 131

[56] References Cited

U.S. PATENT DOCUMENTS

| | | | |
|---|---|---|---|
| 3,941,670 | 3/1976 | Pratt, Jr. | 204/157.61 |
| 4,115,280 | 9/1978 | Pratt, Jr. | 422/186.1 |
| 4,676,880 | 6/1987 | Kramer et al. | 204/157.91 |
| 4,808,285 | 2/1989 | Chen et al. | 204/157.61 |
| 4,822,451 | 4/1989 | Ouderkirk et al. | 204/157.61 |
| 4,880,512 | 11/1989 | Cornelius et al. | 204/157.61 |

FOREIGN PATENT DOCUMENTS

| | | |
|---|---|---|
| 1425340 | 2/1976 | European Pat. Off. |
| 845939 | 8/1960 | United Kingdom ............... 204/901 |

*Primary Examiner*—John Niebling
*Assistant Examiner*—Arun S. Phasge
*Attorney, Agent, or Firm*—Albert W. Hilburger

[57] ABSTRACT

A method and apparatus are disclosed for altering the properties of light sensitive material, for example, biological material, which has a plurality of randomly spaced light absorbing structures thereon. A beam of light, for example, from a laser, is directed, as by scanning, onto a site of the material to be influenced. In order to achieve changes in the properties of the light sensitive material substantially only at each light absorbing structure, the light beam is modulated with a pattern of successive pulses, the pattern being a plurality of pulses of selected duration, energy level, and repetition frequency. The light induced changes may be thermal, mechanical, or chemical in nature.

11 Claims, 2 Drawing Sheets

METHOD AND APPARATUS FOR ALTERING THE PROPERTIES IN LIGHT ABSORBING MATERIAL

This is a continuation of copending application Ser. No. 07/693,678 filed on Apr. 30, 1991, now abandoned.

BACKGROUND OF THE INVENTION

1. Field of the Invention

This invention relates to a device for influencing material using pulsed irradiation.

2. Description of the Prior Art

Devices of this type are known in the literature. According to these publications the known devices comprise a light source and means for directing the beam onto the material to be influenced. The pulse duration of one single pulse determines the spatial extent or magnitude of the light induced effects in the material. Increasing spatial confinement that is, the magnitude of the effects induced in the material by the radiation, requires decreasing pulse durations according to the thermal relaxation time t of the dimension d of a given absorbing structure.

The main limitation of the state of the art concept is that increasing peak irradiations become necessary with decreasing pulse durations in order to achieve a certain amount of light induced effect. High peak irradiations, however, lead to unwanted side effects like localized evaporations or disruptions in the material.

SUMMARY OF THE INVENTION

It is therefore the objective of the invention to apply repetitively multiple pulses of irradiation such that the spatial profile of the absorbed/deposited power densities and/or energy densities are restricted to the absorbing structures and their immediate neighbourhood. Light absorbing structures of a material may be exogenous chromophores and/or pigments artificially imposed onto specific structures of the material. The time course of the deposited/absorbed power densities and/or energy densities at the same time has the highest peak to average modulation at the absorbing sites and decays rapidly with distance. The nonlinear relation between the physical cause (e.g. the temperature increase) and the desired effect (e.g. the coagulation) may lead to an additional increase of spatial confinement. The single pulse energy can always be chosen below the threshold values for side effects such as evaporations or disruptions whereas the degree or intensity of the desired localized effects is caused by the repetitive application of multiple pulses.

These and other aspects of the invention will become more readily apparent upon review of the succeeding disclosure taken in connection with the accompanying drawings. The invention, however, is defined with particularity in the appended claims.

BRIEF DESCRIPTION OF THE DRAWINGS

An embodiment of the invention will now be described by way of example and which reference to the accompanying drawings in which.

DETAILED DESCRIPTION OF THE PREFERRED EMBODIMENTS

Figure 1:
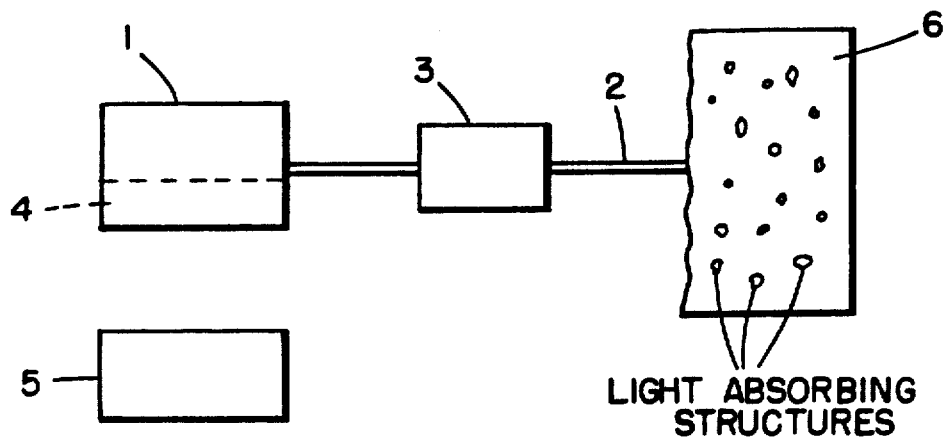
FIG. 1 is a block diagram of the device according to the invention.
Figure 2:
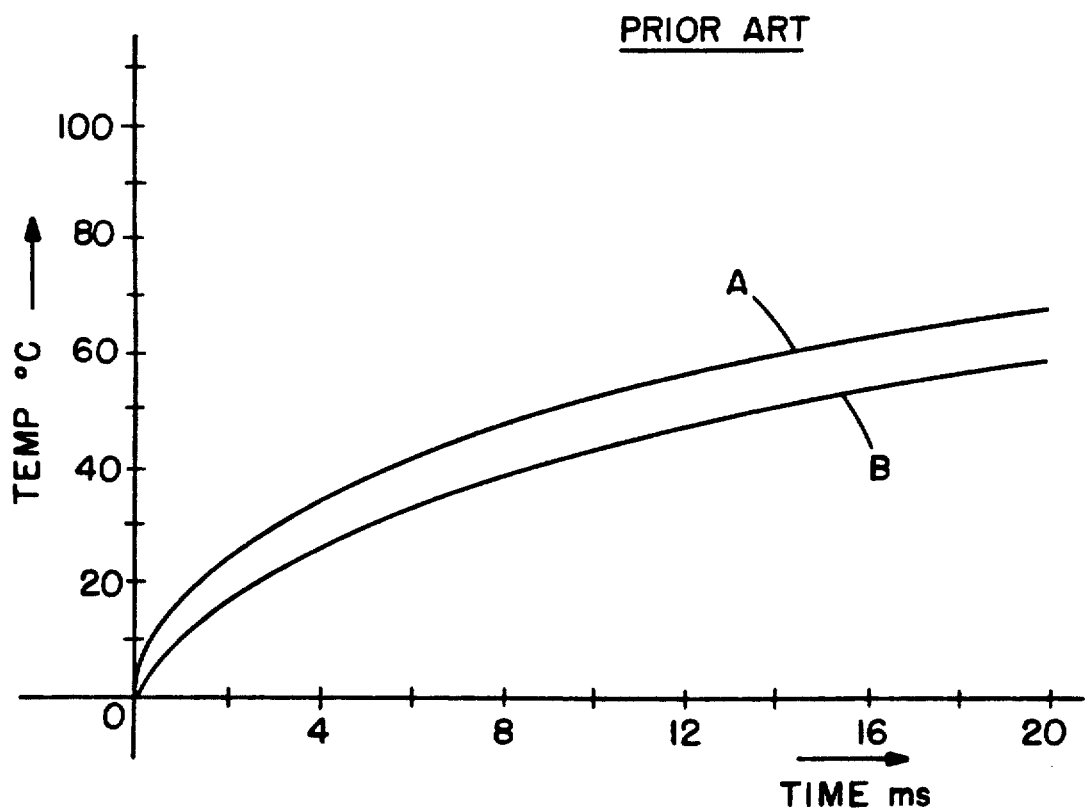
FIG. 2 is a diagram representing the time course of the irradiation induced temperature increase T within (A) and at a distance of 1 μm away (B) from the absorption structure caused by continuous irradiation.
Figure 3:
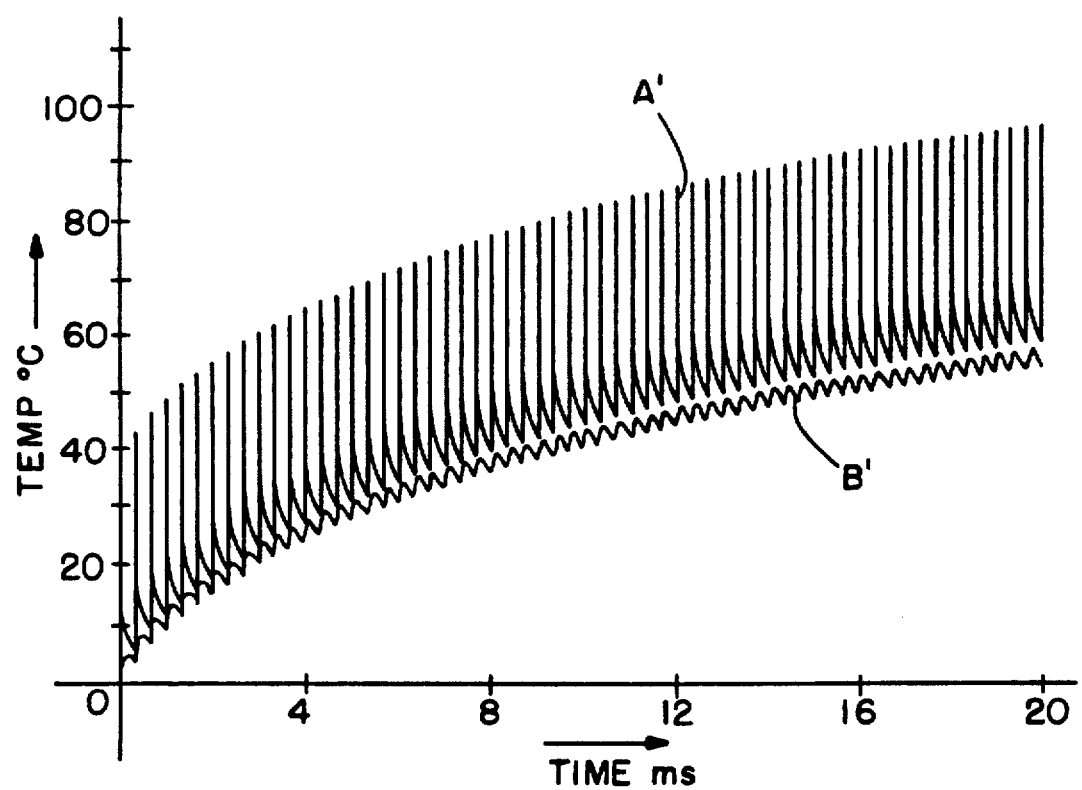
FIG. 3 is a description representing the same situation as in FIG. 2 but caused by repetitive irradiation with multiple light pulses.

The objective of the invention will be described in more detail using FIGS. 1 to 3 of a typical embodiment. FIG. 1 shows a block diagram of a device according to the invention. The device includes a light source (1) and at least one of the modulating means 3, 4, and 5. The light beam (2) is directed onto the material (6) to be influenced and is temporarily or spatially modulated such that a pattern of short light pulses with a given pulse duration, pulse energy, repetition frequency, and number of pulses irradiates the material (6). In case of a continuously emitting light source the following modulating means (3) e.g. an acousto-optical modulator can be used to realize the pulse pattern. If a laser is used as a light source the repetitive pulsed irradiation can be performed using a pulsed pumping power supply (5) and/or an intracavity Q-switching device (4). The single or a combination of modulating means generate a pulse pattern which matches the spectral and spatial distribution of the light absorbing structure in order to achieve the light induced changes of the properties of the material locally only at and around the light absorbing structure as opposed to a homogeneous alteration of the whole irradiated material.

The spirit of the invention is that the irradiation parameters of the pulse pattern e.g. pulse duration, pulse energy, spot size, repetition rate and number of pulses are directly related to the degree of spatial confinement of the irradiation induced changes in relation to the spatial distribution of the light absorbing structures as well as the kind and degree of these changes. FIGS. 2 and 3 typically exemplify the improvement of spatial confinement of repetitive pulsed applications over normal continuous irradiation. FIGS. 2 and 3 show the temperature time course of continuous and repetitively pulsed irradiation respectively. In each figure the temperature time course is shown directly at the absorption structure (upper curve A) as well as 1 μm away from the side of absorption (lower curve B). In both irradiation modalities (FIGS. 2 and 3) the same average power was applied leading to the same average temperature increase. In the case of multiple pulse irradiation (FIG. 3) however the peak temperature at the absorption site is much higher than at the location 1 μm away meaning the "temporal modulation" of the temperature is critically dependent on the location relative to the absorption site. This indicates a high degree of spatial confinement of the highly temperature sensitive thermal affects. In the case of continuous irradiation (FIG. 2) where there is not such a temporal modulation the temperature difference at both locations is—depending on the irradiation geometry—only slightly different. In case of other interaction mechanisms like photomechanical or photochemical effects the same kind of spatial confinement can be achieved due to the localization of the absorbed/deposited power densities or energy densities induced by the repetitive application of multiple pulses of irradiation. This means in general that in the case of repetitively pulsed light application the light induced effects have a much higher localisation if the irradiation parameters e.g. pulse duration, pulse energy, spot size, and repetition rate match the spectral and spatial distribution of the light absorbing structures.

Since the technical means used in the various parts of the block diagram of FIG. 1 are of known conventional type forming no part of the present invention, a detailed description thereof is dispensed with herein for the sake of simplicity.

The invention may be embodied in other specific forms without departing from the spirit of essential characteristics thereof. The embodiment is therefore to be considered in all respects as illustrative and not restrictive.

The common concept of the invention as characterized in the claims is the increase of spatial selectivity of light induced effects due to the repetitive application of multiple light pulses of appropriate irradiation parameters. While preferred embodiments of the invention have been disclosed in detail, it should be understood by those skilled in the art that various other modifications may be made to the illustrated and described embodiments without departing from the scope of the invention as described in the specification and defined in the appended claims.

What is claimed is:

1. A method of coagulating a material which has a plurality of spaced light absorbing structures therein comprising the steps of:

directing a beam of light onto and through the material to be influenced; and pulsing the light beam with a pattern of successive pulses to achieve coagulation of the material substantially only at each light absorbing structure, the pattern of successive light pulses being a plurality of pulses of predetermined number, pulse duration, pulse energy, and repetition rate matched to the spatial distribution and size of the light absorbing structures and to the sensitivity of the material to coagulation.

2. A method as set forth in claim 1 wherein the steps of directing and pulsing the beam of light onto the material to be influenced includes scanning the material with the beam of light to produce a specific exposure duration multiple times at all locations of the material in order to achieve a desired magnitude of change in the properties of the material substantially only at each light absorbing structure.

3. A method as set forth in claim 1 wherein the material to be influenced is biological material.

4. A method as set forth in claim 3 wherein the light absorbing structures of the material to be influenced include at least one of exogenous chromophores and pigments artifically implemented onto specific structures of the material to be influenced.

5. A method as set forth in claim 1 wherein the beam of light provided by a laser.

6. A method as set forth in claim 5 including the step of modulating the beam of light from the laser.

7. A method as set forth in claim 1 wherein the light induced changes in the material to be influenced are thermal in nature.

8. A method as set forth in claim 1 wherein the light induced changes in the material to be influenced are mechanical in nature.

9. A method as set forth in claim 1 wherein the light induced changes in the material to be influenced are chemical in nature.

10. A method as set forth in claim 1 wherein the step of directing the beam of light onto the material to be influenced includes the step of directing the beam of light through an optical system.

11. A method as set forth in claim 10 wherein the optical system used includes fiber optics.

* * * * *